(12) United States Patent
Bencic

(10) Patent No.: US 10,532,080 B2
(45) Date of Patent: *Jan. 14, 2020

(54) SULFOMETHYLATED POLYMIXIN COMPOSITIONS

(71) Applicant: XELLIA PHARMACEUTICALS APS, Copenhagen S (DK)

(72) Inventor: Nenad Bencic, Zagreb (HR)

(73) Assignee: XELLIA PHARMACEUTICALS APS, Copenhagen S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/516,243

(22) PCT Filed: Oct. 1, 2015

(86) PCT No.: PCT/EP2015/072728
§ 371 (c)(1),
(2) Date: Mar. 31, 2017

(87) PCT Pub. No.: WO2016/050928
PCT Pub. Date: Apr. 7, 2016

(65) Prior Publication Data
US 2017/0239321 A1    Aug. 24, 2017

Related U.S. Application Data

(60) Provisional application No. 62/059,711, filed on Oct. 3, 2014.

(51) Int. Cl.
| | | |
|---|---|---|
| *A61K 9/00* | (2006.01) | |
| *A61K 9/08* | (2006.01) | |
| *A61K 38/12* | (2006.01) | |
| *A61K 47/02* | (2006.01) | |

(52) U.S. Cl.
CPC ............ *A61K 38/12* (2013.01); *A61K 9/0019* (2013.01); *A61K 9/0078* (2013.01); *A61K 9/08* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 3,317,506 | A | 5/1967 | Wilkinson |
| 5,767,068 | A | 6/1998 | Vandevanter et al. |
| 2003/0143162 | A1 | 7/2003 | Speirs et al. |
| 2004/0022740 | A1 | 2/2004 | Baker et al. |
| 2008/0066739 | A1 | 3/2008 | Lemahieu et al. |
| 2009/0215677 | A1 | 8/2009 | Vaara et al. |
| 2012/0316105 | A1 | 12/2012 | Magee et al. |
| 2016/0002296 | A1 | 1/2016 | Gunnes et al. |
| 2017/0218024 | A1 | 8/2017 | Bjornstad |
| 2019/0022171 | A1 | 6/2019 | Bencic |

FOREIGN PATENT DOCUMENTS

| | | |
|---|---|---|
| CN | 102531955 A | 7/2012 |
| DE | 1906699 A1 | 2/1970 |
| EP | 1752161 A2 | 2/2007 |
| FR | 1586834 A | 3/1970 |
| WO | 19890009626 A1 | 10/1989 |
| WO | 199820836 | 5/1998 |
| WO | 2008025560 A1 | 3/2008 |
| WO | 2011051070 A1 | 5/2011 |
| WO | 2012168820 A1 | 12/2012 |
| WO | 2014108469 A1 | 7/2014 |
| WO | 2014195405 A1 | 12/2014 |

OTHER PUBLICATIONS

Athanassa et al. "Pharmacokinetics of inhaled colistimethate sodium (CMS) in mechanically ventilated critically ill patients," Intensive Care Med (2012) 38:1779-1786 (Year: 2012).*
BioPharm International ("Biopharmaceutical Manufacturing Using Blow—Fill—Seal Technology," BioPharm International, vol. 24, No. 7, Jul. 1, 2011 (Year: 2011).*
Keller et al. "Performance Characteristics of Colistimethate Sodium Solutions (Colistin) Delivered by Jet Nebulizers compared to the eFlow® SCF Electronic Nebulizer," North American Cystic Fibrosis Conference, St. Louis, USA, Oct. 14-17, 2004 (Year: 2004).*
European Medicines Agency Assessment report of polymixin-based products, EMA/CHMP/153652/2015, dated Feb. 26, 2015.
Suter et al.; "The Sulfomethylation Reaction"; J. Org. Chem.; 10(5); pp. 470-478; (1945).
Healan et al.; "Stability of Colistimethate Sodium in Aqueous Solution"; AAC.ASM.Org; 56(12); pp. 6432-6433; (2012); downloaded Mar. 23, 2017 http://aac.asm.org.
International Search Report and Written Opinion: International Application No. PCT/EP2015/072728; International Filing Date Oct. 1, 2015; dated Nov. 17, 2015; 10 pages.
Wallace et al.; "Self-assembly Behaviour of Colistin and its Prodrug Colistin Methanesulfonate: Implications for Solution Stability and Solubilization"; J. Phys Chem B., Author Manuscript: 114(14); pp. 4836-4840; (2010).
Wallace et al.; "Stability of Colistin Methanesulfonate in Pharmaceutical Products and Solutions for Administration to Patients"; Antimicrobial Agents and Chemotherapy; pp. 3047-3051; (2008).
Kassamali et al.; "Polymyxins: Wisdom Does Not Always Come With Age"; Clinical Infectious Diseases; 57; pp. 877-883; (2013).
Bergen et al.; "Colistin Methanesulfonate Is an Inactive Prodrug of Colistin Against Pseudomonas aeruginosa"; Antimicrobial Agents and Chemotherapy; pp. 1953-1958; (2006).
Bossche et al.; "Identification of Impurities in Polymyxin B and Colistin Bulk Sample Using Liquid Chromatography Coupled to Mass Spectrometry"; Talanta; 82; pp. 1521-1529; (2011).

(Continued)

*Primary Examiner* — Christina Bradley
(74) *Attorney, Agent, or Firm* — Cantor Colburn LLP

(57) ABSTRACT

Disclosed herein is an aqueous solution comprising from 80 mg A/mL to 400 mg A/mL of a sulfomethylated polymyxin and a cartridge containing the same. In addition it is disclosed an aqueous solution for use in therapy.

17 Claims, No Drawings

(56) References Cited

OTHER PUBLICATIONS

European Medicines Agency: "Review Under Article 5(3) of Regulation EC(No) 726-2004; Polymyxin-based products"; retrieved from the Internet: URL:http://www.ema.europa.eu/docs/en_GB/document_library/Report/2015/05/WC500187326.pdf. Retrieved on Sep. 7, 2015.
Govaerts et al.; "Mass Spectrometric Fragmentation of Cyclic Peptides Belonging to the Polymyxin and Colistin Antibiotics Studied by Ion Trap and Quadrupole/Orthogonal-Acceleration Time-of-Flight Technology"; Rapid Comm. in Mass Spectrometry; 16; (2002).
He et al.; "Pharmacokinetics of Four Different Brands of Colistimethate and Formed Colistin in Rats"; J Antimicrob Chemother; 68; pp. 2311-2317; (2013).
Kamin et al.; "Inhalation Solutions—which one are allowed to be mixed? Physico-chemical Coompatibility of Drug Solutions in Nebulizers"; Journal of Cystic Fibrosis; 5; pp. 205-213; (2006).
Li et al.; "Evaluation of Colistin as an Agent Against Multi-resistant Gram-negative Bacteria"; International Journal of Antimicrobial Agents; 25(1); pp. 11-25; (2005).
Li et al.; "Stability of Colistin and Colistin Methanesulfonate in Aqueous Media and Plasma as Determined by High-Performance Liquid Chromatography"; Antimicrobial Agents and Chemotherapy; 47(4); pp. 1364-1370; (2003).
Li et al; "Defining the Dosage Units for Colistin Methanesulfonate: Urgent Need for International Harmonization"; Antimicrobial Agents and Chemotherapy; 50(12); pp. 4231-4232; (2006).
Magee et al,; "Discovery of Dap-3 Polymyxin Analogues for the Treatment of Multidrug-Resistant Gram-Negative Nosocomial Infections"; Journal of Medicinal Chemistry; 53(12); pp. 5079-5093; (2013).
McMillian et al.; "Sodium Colistimethate I: Dissociations of Aminomethanesulfonates in Aqueous Solution"; Journal of Pharmaceutical Sciences; ; 58(6); pp. 730-737; (1969).
Shorin et al. "Antibacterial Activity, Toxicity and Medicinal Properties of Monomycin and Colimycin Methanesulfonates" Database CA [on-line]Chemical Abstracts Service, Columbus; Ohio, Database accession No. 56:38870; 4 pages (1961).
Shorin et al.; "Antibacterial Activity; Toxicity, and Medicinal Properties of Monomycin and Colimycin Methanesulfonates"; Database CA[on-line]Chemical Abstracts Service, Columbus; OH,Database accession No. 56:38870; 4 pages (1961).
Storm et al.; "Polymyxin and Related Peptide Antibiotics"; Annual Review of Biochemistry; 46; pp. 723-763; (1977).
Van den Bossche et al.; "Identification of Impurities in Polymyxin B and Colistin Bulk Sample Using LiquidChromatography Coupled to Mass Spectrometry"; Talanta; 83; pp. 1521-1529; (2011).
Wishart et al.; "1H, 13C and 15N Chemical Shift Referencing in Biomolecular NMR"; Journal of Biomolecular NMR; 6; pp. 135-140; (1995).
Young et al.; "Optimization of Anti-Pseudomonal Antibiotics for Cystic Fibrosis Pulmonary Exacerbations: IV. Colistimethate Sodium"; Pediatric Pulmonology; 48; pp. 1-7; (2013).
Barnett et al.; "Sodium Sulphomethyl Derivatives of Polymyxins"; Birt. J. Pharmacol, 23, pp. 552-574; (1964).
Falagas et al.; "Use of International Units When Dosing Colistin Will Help Decrease Confusion Related to Vrious Formulations of the Drug Around the World"; Antimicrobial Agents and Chemotherapy; pp. 2274-2275; (2006).
Brochet et al.; "Comparative Efficacy of Two Doses of Nebulized Colistimethate for the Eradication of Pseudomonas aeruginosa in Children with Cystic Fibrosis"; Can Respir J; 14(8); pp. 473-479; (2007).
Coly-Mycin M Parenteral (Colistimethate for injection, USP), Prescribing Information as of Feb. 2011; JHP Pharmaceuticals Ref: 300818F, 5 pages.
Yapa et al., Pulmonary and Systemic Pharmacokinetics of Inhaled and Intravenous Colistin Methanesulfonate in Cystic Fibrosis Patients: Targeting Advantage of Inhalation Administration; Antimicrobial Agents arid Chemotherapy; 58(5); pp. 2570-2579; (2014).
USP<1> Particles in Injections; printed Mar. 26, 2019; 4 pages; http://www.uspbpep.com/usp32/pub/data/v32270/usp32nf27s0_c1.html.
Tobramycin Inhalation Solution; printed Mar. 22, 2019; 4 pages; http://www.uspbpep.com/usp32/pub/data/v32270/usp32nf27s)_m83766.html; 4 pages.
Tawde, Suprita A.; "Particulate Matter in Injectables: Main Cause for Recalls"; J. Pharmacovigil; 3(1); e128; 3 pages; (2014).
NonFinal Office Action dated Mar. 4, 2019; U.S. Appl. No. 15/516,286, filed Mar. 31, 2017, 55 pages.
Restriction Requirement dated Nov. 5, 2019; U.S. Appl. No. 15/516,286, filed Mar. 31, 2017; 17 pages.
Final Office Action, U.S. Appl. No. 15/516,286, filed Mar. 31, 2017, dated Sep. 11, 2019, 38 pages.
Li et al.; "Colistin: The Re-emerging Antibiotic for Multidrug-resistant Gram-negative Bacterial Infections"; Lancet Infect Dis; 6; pp. 589-601; (2006).

\* cited by examiner

SULFOMETHYLATED POLYMIXIN COMPOSITIONS

CROSS REFERENCE TO RELATED APPLICATIONS

This application is a National Stage application of PCT/EP2015/072728, filed on Oct. 1, 2015, which claims the benefit of U.S. Provisional Application No. 62/059,711, filed on Oct. 3, 2014 both of which are incorporated by reference in their entirety herein.

FIELD OF THE INVENTION

Disclosed herein is an aqueous solution comprising from 80 mg A/mL to 400 mg A/mL of a sulfomethylated polymyxin and a cartridge containing the same, as well as aqueous solutions for use in therapy.

BACKGROUND

Bacterial lung infection is a major problem and may become life threatening for patients suffering from chronic lung disorders, such as asthma, cystic fibrosis (CF), non CF bronchiectasis and chronic obstructive pulmonary disease. Colistin is a multicomponent polymyxin antibiotic produced by *Bacillus polymyxa* var. *colistinus* that is useful for the treatment of serious bacterial lung infections caused by gram negative bacteria, such as, for example, *Pseudomonas Aeruginosa* or *Klebsiella pneumoniae*. Polymyxin E1 and Polymyxin E2 are the major components of colistin.

When colistin is sulfomethylated, Colistimethate sodium (CMS) can be obtained. In order to become an effective antimicrobial agent, the sulfomethyl groups of CMS need to be hydrolysed thereby liberating free amino-groups. Thus, CMS is considered to be a pro-drug of colistin. The accepted consensus is that in aqueous solutions, CMS spontaneously hydrolyses and forms a complex mixture of sulfomethylated colistin derivatives and possibly colistin. It is widely accepted that a CMS drug product should not contain an amount of colistin considered to be efficacious in vivo because administration of colistin results in noted toxicities.

Coly-Mycin® M Parenteral is a drug containing CMS approved for injection. The label instructs that "parenteral drug products should be inspected visually for particulate matter and discoloration prior to administration, whenever solution and container permit. If these conditions are observed, the product should not be used. [ . . . ] Any final intravenous infusion solution containing colistimethate sodium should be freshly prepared and used for no longer than 24 hours."

Promixin is a drug containing CMS approved for inhalation. The label instructs that "solutions should be used immediately after reconstitution (see section 4.2). Any unused solution remaining in the nebulizer must be discarded following treatment."

A FDA alert published in 2007 following the death of a CF patient linked to the inhalation of an aged CMS solution states that "Premixing colistimethate into an aqueous solution and storing it for longer than 24 hours results in increased concentrations of colistin in solution, increasing the potential for lung toxicity. [ . . . ] In aqueous solution, colistimethate undergoes spontaneous hydrolysis to form colistin."

Several prior art documents try to assess the stability of CMS (Antimicrobial Agents and Chemotherapy, vol. 56, no. 12, December 2012 by Healan et al; J Phys Chem B, vol. 114, no. 14, April 2010 by Wallace et al and Antimicrobial Agents and Chemotherapy, vol. 52, no. 9, September 2008 by Wallace et al) The conclusions drawn from these studies, however, are based on detection of the final hydrolysis products only, namely, colistin A and colistin B. Such methods are not necessarily descriptive of the complex CMS compositions.

In fact, there was no available useful chromatographic method for analyzing CMS when Wallace et al and Healan et al made their studies. However, the method provided by WO 2014/195405 has made it possible to determine the quality and stability of CMS directly.

It has been discovered that an aqueous solution comprising from 80 mg A/mL to 400 mg A/mL of a sulfomethylated polymyxin exhibits physicochemical properties amenable to long-term stability, and may be utilized in the aforementioned therapeutic applications in humans.

SUMMARY

Disclosed herein is an aqueous solution comprising from 80 mg A/mL to 400 mg A/mL of a sulfomethylated polymyxin, for example, colistimethate sodium (CMS) and a cartridge containing the same. Also disclosed are aqueous solutions for use in therapeutic or prophylactic treatment of bacterial infections in the pulmonary system.

DETAILED DESCRIPTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Numerals used herein referring to a physicochemical property, time, temperature, concentration, and the like, are understood to represent measured values, and, as such, should not be strictly construed as being absolute, but rather be construed so as to account for experimental error and rounding. For example, a temperature value of 2° C. will be understood to have a certain degree of variance based on the instrument used to measure the temperature, e.g., glass thermometer, digital thermometer, etc. Moreover, a measured temperature of 1.6° C., when rounded up, would be equivalent to a temperature value of 2° C.

The term "chromatographic profile," as used herein, means an HPLC chromatogram obtained by a method capable of separating or display at least 50 peaks present in CMS. Such method can be found in WO 2014/195405.

The term "no significant change in the chromatographic profile" is meant to include chromatograms in which the relative peak intensity is relatively stable, for example, varies less than 5%, or more preferably, less than 2%.

The term "physicochemical property," as used herein, means a parameter that is a measure of a physicochemical property, such as, for example, sub-visible particles, number of visible particles, color, clarity, pH, osmolality, turbidity, or viscosity.

The approximate relationship between colistin base activity per volume, and the resultant antibacterial activity of the solution as measured in International Units per mL (IU/mL) is shown in Table 1 below. The activity of CMS depends on the potency measured and the water content.

TABLE 1

| Colistin base activity per mL (mg A/mL) | Million International units per mL (MIU/mL) |
|---|---|
| 0.4 | 0.0125 |
| 37.5 | 1.125 |
| 75 | 2.25 |
| 112.5 | 3.375 |
| 150 | 4.5 |

The term "colistin base activity" is alternatively referred to herein as "A". According to the FDA-approved Coly-Mycin M label from January 2013, colistimethate sodium is supplied in vials containing 150 mg colistin base activity. The vials should be reconstituted with 2 mL sterile water for injection to provide colistimethate sodium at a concentration equivalent to 75 mg/mL colistin base activity. In the present disclosure, we consider such solutions to contain 75 mg A/mL of CMS. Dissolving 3.0 MIU of CMS in 1.0 ml water will provide 100 mg A/mL of CMS. Dissolving 2.8 MIU of CMS in 1.0 ml water will provide 94 mg A/mL of CMS.

The term "aqueous solution" as used herein, means a solution in which water is the principle (or majority) solvent. Suitable aqueous solutions for sulfomethylated polymyxins include, but are not limited to water for injection (WFI), ultrapure water, 0.9% saline solution and 0.45% saline solution.

The term "CMS" as described herein refers to a composition comprising sulfomethylated polymyxin E1 and sulfomethylated polymyxin E2. The Chemical Abstracts Registry (CAS) has assigned such a composition the number 8068-28-8 for CMS. In general, CMS is considered to be the mixture of sulfomethylated colistin.

The term "colistin" as described herein refers to a composition comprising polymyxin E1 and polymyxin E2. Chemical abstracts have assigned the number 1066-17-7 for colistin. According to the European Pharmacopoeia, colistin should comprise more than 77% of Polymyxin E1, E2, E3, E1i and E1-7MOA, but less than 10% of each of the minor components Polymyxin E3, E1-i and E1-MOA.

The term "Polymyxin E" as described herein is used interchangeably with "colistin".

The term "Polymyxin E1" as described herein refers to the compound having the CAS no 7722-44-3. Polymyxin E1 is used interchangeably with colistin A.

The term "Polymyxin E2" as described herein refers to the compound having the CAS no 7239-48-7. Polymyxin E2 is used interchangeably with colistin B.

The term "Polymyxin B" as used herein, refers to the compound having the CAS no. 1405-20-5.

The term "sulfomethylated polymyxin" as used herein refers to a polymyxin comprising at least one sulfomethyl ($-CH_2S(O)_2OR^3$) group attached to a γ-amino group on an L-DAB (or L-DBU) residue, which the $R^3$ radical can be H or M, where M is a monovalent cation, which refers to a cationic species containing a single positive charge, examples of which include, but are not limited to $Li^+$, $Na^+$, $K^+$, $H_mN(C_{1-4}alkyl)_n^+$, where m is 0-4 and n is 0-4 with the proviso that m+n=4.

The term "DAB" as described herein, refers the radical derived from 2,4-diaminobutanoic acid, in which the carbon atom adjacent to the carbonyl carbon (i.e., the α-carbon) has a stereochemistry designated as the L-configuration. L-DAB is alternatively referred to in the literature as L-DBU.

The most common sulfomethylated polymyxin is called CMS, but other sulfomethylated polymyxins exist, for example, sulfomethylated Polymyxin B, sulfomethylated Polymyxin E1, sulfomethylated Polymyxin E2 etc. Sulfomethylated polymyxins are also disclosed in PCT published application WO 2014/108469 (Xellia), the subject matter of which is incorporated by reference in its entirety. Additional polymyxins are described in PCT published application WO 2012/168820, which corresponds to US 2012/0316105, the subject matter of which is incorporated by reference in its entirety.

The term "cartridge," as used herein means a vessel suitable for storage of aqueous solutions comprising sulfomethylated polymyxins.

The term "mOsm/kg," as related to osmolality, as used herein means milliosmole per kg.

The term "NTU," as related to turbidity, as used herein means Nephelometric Turbidity Units.

The term "USP <No.>," as used herein refers to a specifically numbered monograph, as described in The United States Pharmacopeia (USP 35, May 1, 2012).

The term "Ph. Eur.," followed by a designated numeric code, as used herein, refers to the European Pharmacopoeia, Eight Edition, Volume 1, 2013.

"pH" Is the conventional measurement unit for hydrogen ion activity in a solution at 25° C. unless other temperature is specified. The suitable pH range for the aqueous CMS solutions in the cartridges according to the present invention is 6-9, such as 6.5-8.5. The most preferred pH range for the aqueous CMS solutions in the cartridges according to the present invention is 6.0-7.0.

A first embodiment is directed to an aqueous solution comprising from 80 mg A/mL to 400 mg A/mL of a sulfomethylated polymyxin, and all concentrations included in said range, such as, 80 mg A/mL, 90 mg A/mL, 100 mg A/mL, 110 mg A/mL, 120 mg A/mL, 130 mg A/mL, 140 mg A/mL, 150 mg A/mL, 160 mg A/mL, 170 mg A/mL, 180 mg A/mL, 190 mg A/mL, 200 mg A/mL, 210 mg A/mL, 220 mg A/mL, 230 mg A/mL, 240 mg A/mL, 250 mg A/mL, 260 mg A/mL, 270 mg A/mL, 280 mg A/mL, 290 mg A/mL, 300 mg A/mL, 310 mg A/mL, 320 mg A/mL, 330 mg A/mL, 340 mg A/mL, 350 mg A/mL, 360 mg A/mL, 370 mg A/mL, 380 mg A/mL, 390 mg A/mL, and 400 mg A/mL.

In a first aspect of the first embodiment, the aqueous solution comprises from 90 to 200 mg A/mL, and all concentrations included in said range, such as, 90 mg A/mL, 100 mg A/mL, 110 mg A/mL, 120 mg A/mL, 130 mg A/mL, 140 mg A/mL, 150 mg A/mL, 160 mg A/mL, 170 mg A/mL, 180 mg A/mL, 190 mg A/mL, and 200 mg A/mL.

In a second aspect of the first embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a third aspect of the first embodiment, the aqueous solution contains an acceptable amount of foreign matter as determined by USP <1>.

In a fourth aspect of the first embodiment, the aqueous solution is free of visible particles, as determined by USP <1>.

In a fifth aspect of the first embodiment, the aqueous solution has an acceptable clarity, as determined by USP <1>.

In a sixth aspect of the first embodiment, the aqueous solution has a turbidity of not more than 3 NTU, as determined by Ph. Eur. 2.2.1.

In a seventh aspect of the first embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an eighth aspect of the first embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a ninth aspect of the first embodiment, the aqueous solution further comprises from 0 to 0.9% w/v NaCl, and all concentrations included in said range, such as, 0% w/v NaCl, 0.10% w/v NaCl, 0.15% w/v NaCl, 0.20% w/v NaCl, 0.25% w/v NaCl, 0.30% w/v NaCl, 0.35% w/v NaCl, 0.40% w/v NaCl, 0.45% w/v NaCl, 0.50% w/v NaCl, 0.55% w/v NaCl, 0.60% w/v NaCl, 0.65% w/v NaCl, 0.70% w/v NaCl, 0.75% w/v NaCl, 0.80% w/v NaCl, 0.85% w/v NaCl, and 0.90% w/v NaCl.

In a 10th aspect of the first embodiment, the aqueous solution has an osmolality from 500 to 1300 mOsm/kg, and all values included in said range, such as, 500 mOsm/kg, 550 mOsm/kg, 600 mOsm/kg, 650 mOsm/kg, 700 mOsm/kg, 750 mOsm/kg, 800 mOsm/kg, 850 mOsm/kg, 900 mOsm/kg, 950 mOsm/kg, 1000 mOsm/kg, 1050 mOsm/kg, 1100 mOsm/kg, 1150 mOsm/kg, 1200 mOsm/kg, 1250 mOsm/kg, and 1300 mOsm/kg.

In a 11th aspect of the first embodiment, the aqueous solution has an osmolality from 700 to 1200 mOsm/kg, and all values included in said range, such as, 700 mOsm/kg, 750 mOsm/kg, 800 mOsm/kg, 850 mOsm/kg, 900 mOsm/kg, 950 mOsm/kg, 1000 mOsm/kg, 1050 mOsm/kg, 1100 mOsm/kg, 1150 mOsm/kg, and 1200 mOsm/kg.

In a 12th aspect of the first embodiment, the aqueous solution has an osmolality from 900 to 1200 mOsm/kg, and all values included in said range, such as, 900 mOsm/kg, 950 mOsm/kg, 1000 mOsm/kg, 1050 mOsm/kg, 1100 mOsm/kg, 1150 mOsm/kg, and 1200 mOsm/kg.

In a 13th aspect of the first embodiment, the aqueous solution has a pH from 6 to 8, and all values included in said range, such as, 6, 6.5, 7, 7.5, and 8.

A second embodiment is directed to a cartridge that comprises an aqueous solution comprising from 80 mg A/mL to 400 mg A/mL of a sulfomethylated polymyxin, and all concentrations mentioned above.

In a first aspect of the second embodiment, the aqueous solution comprises from 90 to 200 mg A/mL, and all concentrations included in said range, such as, 90 mg A/mL, 100 mg A/mL, 110 mg A/mL, 120 mg A/mL, 130 mg A/mL, 140 mg A/mL, 150 mg A/mL, 160 mg A/mL, 170 mg A/mL, 180 mg A/mL, 190 mg A/mL, and 200 mg A/mL.

In a second aspect of the second embodiment, the aqueous solution comprises from 90 to 120 mg A/mL, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a third aspect of the second embodiment, the aqueous solution contains an acceptable amount of foreign matter as determined by USP <1>.

In a fourth aspect of the second embodiment, the aqueous solution is free of visible particles, as determined by USP <1>.

In a fifth aspect of the second embodiment, the aqueous solution has an acceptable clarity, as determined by USP <1>.

In a sixth aspect of the second embodiment, the aqueous solution has a turbidity of not more than 3 NTU, as determined by Ph. Eur. 2.2.1.

In a seventh aspect of the second embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an eighth aspect of the second embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a ninth aspect of the second embodiment, the cartridge is a glass ampoule, ready to use-syringe or a blow-fill sealed vessel.

In a 10th aspect of the second embodiment, the aqueous solution further comprises from 0 to 0.9% w/v NaCl, and all concentrations included in said range, such as, 0% w/v NaCl, 0.10% w/v NaCl, 0.15% w/v NaCl, 0.20% w/v NaCl, 0.25% w/v NaCl, 0.30% w/v NaCl, 0.35% w/v NaCl, 0.40% w/v NaCl, 0.45% w/v NaCl, 0.50% w/v NaCl, 0.55% w/v NaCl, 0.60% w/v NaCl, 0.65% w/v NaCl, 0.70% w/v NaCl, 0.75% w/v NaCl, 0.80% w/v NaCl, 0.85% w/v NaCl, and 0.90% w/v NaCl.

In an 11th aspect of the second embodiment, the aqueous solution has an osmolality from 500 to 1300 mOsm/kg, and all values included in said range, such as, 500 mOsm/kg, 550 mOsm/kg, 600 mOsm/kg, 650 mOsm/kg, 700 mOsm/kg, 750 mOsm/kg, 800 mOsm/kg, 850 mOsm/kg, 900 mOsm/kg, 950 mOsm/kg, 1000 mOsm/kg, 1050 mOsm/kg, 1100 mOsm/kg, 1150 mOsm/kg, 1200 mOsm/kg, 1250 mOsm/kg, and 1300 mOsm/kg.

In a 12th aspect of the second embodiment, the aqueous solution has an osmolality from 700 to 1200 mOsm/kg, and all values included in said range, such as, 700 mOsm/kg, 750 mOsm/kg, 800 mOsm/kg, 850 mOsm/kg, 900 mOsm/kg, 950 mOsm/kg, 1000 mOsm/kg, 1050 mOsm/kg, 1100 mOsm/kg, 1150 mOsm/kg, and 1200 mOsm/kg.

In a 13th aspect of the second embodiment, the aqueous solution has an osmolality from 900 to 1200 mOsm/kg, and all values included in said range, such as, 900 mOsm/kg, 950 mOsm/kg, 1000 mOsm/kg, 1050 mOsm/kg, 1100 mOsm/kg, 1150 mOsm/kg, and 1200 mOsm/kg.

In a 14th aspect of the second embodiment, the aqueous solution has a pH from 6 to 8, and all values included in said range, such as, 6, 6.5, 7, 7.5, and 8.

A third embodiment is directed to an aqueous solution comprising from 80 mg A/mL to 300 mg A/mL of CMS.

In a second aspect of the first embodiment, the aqueous solution has a pH of 6-8.

In a third aspect of the third embodiment, the aqueous solution contains an acceptable amount of foreign matter as determined by USP <1>.

In a fourth aspect of the third embodiment, the aqueous solution is free of visible particles, as determined by USP <1>.

In a fifth aspect of the third embodiment, the aqueous solution has an acceptable clarity, as determined by USP <1>.

In a sixth aspect of the third embodiment, the aqueous solution has a turbidity of not more than 3 NTU, as determined by Ph. Eur. 2.2.1.

In a seventh aspect of the third embodiment, the aqueous solution has a pH of 6-8, the solution contains an acceptable amount of foreign matter as determined by USP <1>; the solution is free of visible particles, as determined by USP <1>, the solution has an acceptable clarity, as determined by USP <1> and the solution has a turbidity of not more than 3 NTU, as determined by Ph. Eur. 2.2.1.

In a eighth aspect of the third embodiment, the aqueous solution comprises 85 mg A/mL-150 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

In a nineth aspect of the third embodiment, the aqueous solution comprises 90 mg A/mL-120 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

In a tenth aspect of the third embodiment, the aqueous solution comprises 90 mg A/mL-110 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

In an eleventh aspect of the third embodiment, the aqueous solution comprises approximately 95 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

A fourth embodiment is directed to a cartridge containing an aqueous solution comprising 80 mg A/mL to 300 mg A/mL of CMS.

In a second aspect of the fourth embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an third aspect of the fourth embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a fourth aspect of the fourth embodiment, the cartridge is a glass ampoule, ready-to use-syringe or a blow-fill sealed vessel.

In a fifth aspect of the fourth embodiment, the aqueous solution has a pH of 6-8, the solution contains an acceptable amount of foreign matter as determined by USP <1>; the solution is free of visible particles, as determined by USP <1>, the solution has an acceptable clarity, as determined by USP <1> and the solution has a turbidity of not more than 3 NTU, as determined by Ph. Eur. 2.2.1.

In a sixth aspect of the fourth embodiment, the aqueous solution comprises 85 mg A/mL-150 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

In a seventh aspect of the fourth embodiment, the aqueous solution comprises 90 mg A/mL-120 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

In an eighth aspect of the fourth embodiment, the aqueous solution comprises 90 mg A/mL-110 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

In an ninth aspect of the fourth embodiment, the aqueous solution comprises approximately 95 mg A/mL of CMS; it has a pH of 6-8; the solution contains an acceptable amount of foreign matter as determined by USP <1>; the solution is free of visible particles, as determined by USP <1>; the solution has an acceptable clarity, as determined by USP <1> and the solution has a turbidity of not more than 3 NTU, as determined by Ph. Eur. 2.2.1.

A further embodiment is directed to an aqueous solution comprising from 80 to 300 mg A/mL of a sulfomethylated polymyxin for use in treatment of bacterial infections in the pulmonary system by pulmonary administration.

Every embodiments and aspects concerning the aqueous solution as described herein is applicable for medical use according to this embodiment.

In one aspect of this embodiment the aqueous solution as described in the aforementioned aspects and embodiments is for use in treatment of serious bacterial lung infections caused by gram negative bacteria, such as, for example, *Pseudomonas Aeruginosa* or *Klebsiella pneumoniae*.

In another aspect of this embodiment the aqueous solution is a ready-to-use composition, suitable for long-term storage, for use in treatment of infections in the pulmonary system and/or suitable for example in a parenteral, a nasal, and/or an inhalation application.

EXAMPLES

Not to be limited by way of example, the following examples serve to facilitate a better understanding of the subject matter disclosed herein.

Example 1

Three aqueous solutions comprising colistimethate sodium (CMS) at three different concentrations (37.5 mg A/mL, 75 mg A/mL, and 112.5 mg A/mL) were stored in airtight containers over a 1-week period of time.

The HPLC-chromatographic profile (data not shown) showed degradation in an aqueous solution comprising 37.5 mg A/mL of CMS, but no significant degradation in an aqueous solution comprising either 75 mg A/mL of CMS or 112.5 mg A/mL of CMS.

Several parameters of the above-mentioned compositions were observed over the stated time period at temperatures (5° C. (data not shown), 25° C., 30° C., and 40° C.), which include, but are not limited to: appearance, foreign matter (USP <1>, the presence of visible particles ("VP") is non-compliant), clarity of solution (USP <1>, lack of clarity results in non-compliance), number of subvisible particles (both ≤10 μm and ≤25 μm, USP <788>), pH (USP <791>), osmolality (USP <785>), and turbidity (Ph. Eur. 2.2.1). The results of these observations are presented in Table 2.

TABLE 2

| Parameter | 37.5 mg A/mL | | | 75 mg A/mL | | | 112.5 mg A/mL | | |
|---|---|---|---|---|---|---|---|---|---|
| | 25° C. | 30° C. | 40° C. | 25° C. | 30° C. | 40° C. | 25° C. | 30° C. | 40° C. |
| Appearance[a] | SYS[h] | SYS[h] | SYS[h] | SYS[h] | SYS[h] | SYS[h] | SYS[h] | SYS[h] | SYS[h] |
| Foreign Matter[b] | VP[i] | VP[i] | VP[i] | C[j] | VP[i] | VP[i] | C[j] | C[j] | C[j] |
| Clarity[c] | NC[k] | NC[k] | NC[k] | C[j] | NC[k] | NC[k] | C[j] | C[j] | C[j] |
| PN[d] ≤10 μm[e] | 217 | 185 | 275 | 469 | 129 | 176 | 93 | 74 | 144 |
| PN[d] ≤25 μm[f] | 4 | 6 | 3 | 14 | 1 | 6 | 5 | 2 | 4 |
| pH | 6.81 | 6.83 | 6.88 | 6.35 | 6.44 | 6.46 | 6.07 | 6.13 | 6.17 |
| Osmolality (Osm/kg) | 0.311 | 0.306 | 0.282 | 0.667 | 0.667 | 0.642 | 1.117 | 1.160 | 1.143 |
| Turbidity[g] | 3.60 | 6.26 | 1.32 | 1.96 | 0.68 | 0.50 | 0.50 | 0.64 | 1.03 |

Specification and Notes Legend
[a]Colorless to slightly yellow solution,
[b]Free from visible particles,
[c]The solution is not significantly less clear than an equal volume of purified Water contained in a similar vessel and examined similarly.
[d]Number of sub-divisible particles (PN),
[e]Not more than ("NMT") 3000/mL,
[f]NMT 300/mL,
[g]NMT 3 NTU,
[h]Slightly yellow solution (SYS),
[i]Visible Particles (VP),
[j]Complies (C),
[k]Not clear (NC).

From this data, it can be seen that an aqueous solution having a concentration of 75 mg A/mL of CMS exhibited an unacceptable amount of foreign matter, clarity, and/or turbidity, and thus, may not be suitable for long-term storage as a ready-to-use composition, as related, to, for example, a parenteral, a nasal, and, an inhalation solution. This should be contrasted to an aqueous solution having a higher concentration e.g. 112.5 mg A/mL of CMS which exhibited an acceptable amount of foreign matter, clarity, and turbidity. The stability studies were extended over a period of 3-months. The results of these studies (25° C.) are summarized in Table 3.

concentrations may be suitable for long-term storage as a ready-to-use compositions, and thus, may be used in a cartridge suitable for parenteral, nasal, inhalation application.

As stated above, the package insert for the Coly-Mycin® M Parenteral drug product states that "[p]arenteral drug products should be inspected visually for particulate matter and discoloration prior to administration, whenever solution and container permit," and that "[i]f these conditions are observed, the product should not be used."

Accordingly, an unexpected and surprising result of the embodiments described herein is that the aqueous solution is

TABLE 3

| Parameter | 37.5 mg A/mL | | | 75 mg A/mL | | | 112.5 mg A/mL | | |
|---|---|---|---|---|---|---|---|---|---|
| | 1-wk | 1-mo | 3-mo | 1-wk | 1-mo | 3-mo | 1-wk | 1-mo | 3-mo |
| Appearance[a] | SYS[h] | SYS[h] | SYS[h] | SYS[h] | SYS[h] | SYS[h] | SYS[h] | SYS[h] | SYS[h] |
| Foreign Matter[b] | VP[i] | VP[i] | VP[i] | C[j] | VP[i] | VP[i] | C[j] | C[j] | C[j,l] |
| Clarity[c] | NC[k] | C[j] | NC[k] | C[j] | C[j] | NC[k] | C[j] | C[j] | C[j] |
| PN[d] ≤10 μm[e] | 217 | 50 | 54 | 469 | 50 | 68 | 93 | 23 | 55 |
| PN[d] ≤25 μm[f] | 4 | 5 | 2 | 14 | 3 | 1 | 5 | 2 | 2 |
| pH | 6.81 | 6.82 | 6.90 | 6.35 | 6.34 | 6.43 | 6.07 | 6.03 | 6.13 |
| Osmolality (Osm/kg) | 0.311 | 0.308 | 0.299 | 0.667 | 0.678 | 0.649 | 1.177 | 1.162 | 1.130 |
| Turbidity[g] | 3.60 | 3.69 | 1.42 | 1.96 | 1.97 | 0.38 | 0.50 | 0.46 | 0.46 |

Specification and Notes Legend
[a]Colorless to slightly yellow solution,
[b]Free from visible particles,
[c]The solution is not significantly less clear than an equal volume of purified Water contained in a similar vessel and examined similarly.
[d]Number of sub-divisible particles (PN) less than or equal to the stated value,
[e]Not more than ("NMT") 3000/mL,
[f]NMT 300 /mL,
[g]NMT 3 NTU,
[h]Slightly yellow solution (SYS),
[i]Visible Particles (VP),
[j]Complies (C),
[k]Not clear (NC),
[l]3 of 5 vials showed no particles, with the 2 vials showed what appeared to be microbial growth.

The results in this table confirm that an aqueous solution having a concentration less than 75 mg A/mL of CMS may not be suitable for long-term storage as a ready-to-use composition, but that aqueous solutions having a higher free of visible particles, as determined by USP <1>, has an acceptable clarity, as determined by USP <1>; and has a turbidity of not more than 3 NTU, as determined by Ph. Eur. 2.2.1.

Example 2

Aqueous solutions comprising 94 mg A/mL colistimethate sodium (CMS) were stored in airtight containers for 1-month at different temperatures (5° C., 25° C., 30° C., and 40° C.). The HPLC-chromatographic profile (data not shown) showed no significant change.

Several parameters of the above-mentioned composition were observed over the 1-month period of time, the results are summarized in Table 4.

TABLE 4

| Parameter | Initial | 5° C. | 25° C. | 30° C. | 40° C. |
|---|---|---|---|---|---|
| Appearance[a] | SYS[h] | SYS[h] | SYS[h] | SYS[h] | SYS[h] |
| Foreign Matter[b] | C[j] | C[j] | C[j] | C[j] | C[j] |
| Clarity[c] | C[j] | C[j] | C[j] | C[j] | C[j] |
| PN[d] ≤10 μm[e] | 102 | 11 | 34 | 33 | 59 |
| PN[d] ≤25 μm[f] | 2 | 0 | 2 | 3 | 1 |
| pH | 6.21 | 5.98 | 6.09 | 6.11 | 6.13 |
| Osmolality (Osm/kg) | 0.928 | 0.916 | 0.925 | 0.908 | 0.929 |
| Turbidity[g] | 0.4 | 0.3 | 0.3 | 0.4 | 0.4 |

Specification and Notes Legend
[a]Colorless to slightly yellow solution,
[b]Free from visible particles,
[c]The solution is not significantly less clear than an equal volume of purified Water contained in a similar vessel and examined similarly.
[d]Number of sub-divisible particles (PN),
[e]Not more than ("NMT") 3000/mL,
[f]NMT 300/mL,
[g]NMT 3 NTU,
[h]Slightly yellow solution (SYS),
[i]Visible Particles (VP),
[j]Complies (C),
[k]Not clear (NC).

The results in this table confirm that a composition having a concentration of 94 mg A/mL of CMS may be suitable for long-term storage as a ready-to-use composition.

Observations for aqueous solutions comprising 94 mg A/mL or 112 mg A/mL of colistimethate sodium (CMS) (data not shown) confirm that a composition having a concentration greater than 75 mg A/mL CMS may be suitable for long-term storage as a ready-to-use composition.

Example 3

Viscosity values for compositions comprising CMS at various compositions were measured at 25° C. and the results are summarized in Table 5.

TABLE 5

| Sample | Conc. (mg A/ml) | Viscosity (cSt) |
|---|---|---|
| Water | 0.0 | 0.94 |
| 1 | 37.5 | 1.25 |
| 2 | 75.0 | 1.89 |
| 3 | 94.0 | 2.24 |
| 4 | 112.5 | 3.05 |

The plotted viscosity ($\eta$) values versus concentration (c) values showed a quadratic relationship ($\eta = Ac^2 + Bc + C$) with a good agreement ($R^2 = 0.9901$), in which $A = 0.0002$, $B = 0.0003$, and $C = 0.9642$.

In view of the functional relationship presented above, an additional aspect of the first and second embodiments is a composition comprising a sulfomethylated polymyxin having viscosity values as determined by the above-mentioned quadratic expression.

Although a full and complete description is believed to be contained herein, certain patent and non-patent references, including the above-mentioned USP and Ph. Eur. Monographs, may include certain essential subject matter. To the extent that these patent and non-patent references describe essential subject matter, these references are hereby incorporated by reference in their entirety. It is understood that the meanings of the incorporated subject matter are subservient to the meanings of the subject matter disclosed herein.

The invention claimed is:

1. An aqueous solution comprising 80 mg A/mL to 400 mg A/mL of a sulfomethylated polymyxin,
   wherein the solution is free from visible particles after storage for 3 months at 25° C.

2. The solution according to claim 1, comprising 80 mg A/mL to 300 mg A/mL of colistimethate sodium.

3. The solution according to claim 2, comprising 85 mg A/mL to 150 mg A/mL of colistimethate sodium.

4. The solution according to claim 3, comprising 90 mg A/mL to 120 mg A/mL of colistimethate sodium.

5. A cartridge comprising the solution of claim 1.

6. The cartridge according to claim 5, which is a glass ampoule, ready-to-use syringe or a blow-fill sealed vessel.

7. The cartridge of claim 5, wherein the aqueous solution comprises 0% w/v NaCl to 0.9% w/v NaCl.

8. The cartridge of claim 5, wherein the aqueous solution has an osmolality of 500 mOsm/kg to 1300 mOsm/kg.

9. The cartridge of claim 5, wherein the aqueous solution has a pH of 6 to 9.

10. The cartridge of claim 5, wherein the aqueous solution has a pH of 6 to 7.

11. A method of therapeutic or prophylactic treatment of bacterial infection in the pulmonary system of a human comprising administering the aqueous solution of claim 1.

12. The cartridge of claim 5, wherein the solution comprises 80 mg A/mL to 300 mg A/mL of colistimethate sodium.

13. The cartridge of claim 5, wherein the solution comprises 85 mg A/mL to 150 mg A/mL of colistimethate sodium.

14. The cartridge of claim 5, wherein the solution comprises 90 mg A/mL to 120 mg A/mL of colistimethate sodium.

15. The method of claim 11, wherein the solution comprises 80 mg A/mL to 300 mg A/mL of colistimethate sodium.

16. The method of claim 11, wherein the solution comprises 85 mg A/mL to 150 mg A/mL of colistimethate sodium.

17. The method of claim 11, wherein the solution comprises 90 mg A/mL to 120 mg A/mL of colistimethate sodium.

\* \* \* \* \*